United States Patent [19]
Liao et al.

[11] Patent Number: 5,717,049
[45] Date of Patent: Feb. 10, 1998

[54] HIGH REFRACTIVE INDEX HYDROGELS PREPARED FROM POLYMERS AND COPOLYMERS OF N-BENZYL-N-METHYLACRYLAMIDE

[75] Inventors: Xiugao Liao, Irvine; Yading Wang, Mission Viejo; Stephen Q. Zhou, Irvine, all of Calif.

[73] Assignee: Pharmacia Iovision, Inc., Irvine, Calif.

[21] Appl. No.: 622,527

[22] Filed: Mar. 25, 1996

[51] Int. Cl.$^6$ ........................................ C08F 20/58
[52] U.S. Cl. .................... 526/304; 623/6; 524/555
[58] Field of Search ...................... 526/303.1, 304; 623/6; 524/555

[56] References Cited

U.S. PATENT DOCUMENTS

| | | |
|---|---|---|
| 4,337,332 | 6/1982 | Melancon et al. |
| 5,439,950 | 8/1995 | Liao et al. ............................ 523/108 |
| 5,480,950 | 1/1996 | Wang et al. ............................ 526/258 |

FOREIGN PATENT DOCUMENTS 0855741  12/1960  United Kingdom .................. 526/304

OTHER PUBLICATIONS

"Nitrosation of xβ Unsat. Carboxamide with Nitric Oxide and Triethylsilane Catalyzed by Cobalt (II) Complex" Kato et al. Chem Lett. (1990) (8), 1395–8.
Process Technol. Lab. 3M Cent. Res. St. Paul, Minnesota, USA Radiat. Phys Chem (1985), 25 (4–6), 483–90 abstract.

*Primary Examiner*—Joseph L. Schofer
*Assistant Examiner*—N. Sarofim
*Attorney, Agent, or Firm*—Oppenheimer Poms Smith

[57] ABSTRACT

Novel biocompatible, high strength hydrogels useful in intraocular lenses are provided which are optically transparent, have high refractive indices and possess long term stability. The hydrogels are prepared from cross-linked copolymers of N-benzyl-N-methylacrylamide.

18 Claims, No Drawings

HIGH REFRACTIVE INDEX HYDROGELS PREPARED FROM POLYMERS AND COPOLYMERS OF N-BENZYL-N-METHYLACRYLAMIDE

BACKGROUND OF THE INVENTION

1. Field of the Invention

The present invention relates to hydrogels. More particularly, this invention relates to optically transparent, high refractive index, high strength hydrogels which are especially useful in the fabrication of intraocular lenses. In one of its more particular aspects, this invention relates to a novel monomer for use in producing such hydrogels. In another of its more particular aspects, the present invention relates to intraocular lenses prepared from such hydrogels.

2. Description of Related Art

Since the early 1940s, optical devices in the form of intraocular lenses have been utilized to replace the natural physiological crystalline ocular lens in humans and other mammals. Typically, the intraocular lens is implanted within the ocular environment immediately after surgically removing the natural lens which has become opaque or otherwise damaged by cataract formation or injury.

For decades the most prevalently utilized materials for forming intraocular lenses were acrylates or methacrylates and particularly polymethylmethacrylate, a rigid, glassy polymer. However, since full-size polymethylmethacrylate intraocular lenses have diameters in the range of 8–13 mm, relatively large incisions were necessary in order to remove the natural lens and insert the intraocular lens.

Recently developed surgical techniques and improved instrumentation have made it possible to remove the opaque or damaged natural lens through incision sizes as small as 2–3 mm. Because small incision surgery is much less traumatic for patients and decreases complications and healing time, this technique has become the method of choice for a large number of ophthalmic surgeons.

A number of different intraocular lens designs and materials have been developed for use in connection with small incision surgical techniques. One approach utilizes the concept of preparing lenses from elastomeric materials such as silicones and thermoplastic polymers. Prior to surgically inserting the elastomeric lens, the surgeon rolls or folds the lens so that it is reduced in size for passing into the eye through a smaller incision. Once placed within the eye, the lens unfolds or unrolls to its full size.

One problem associated with these elastomeric lenses is the possibility that permanent deformation or crease marks may occur when the lens is folded or rolled. This is especially a concern at the center of the lens optical zone where most of the rolling or folding deformation takes place.

Another approach to providing a small incision intraocular lens is suggested in U.S. Pat. No. 4,731,079. This reference discloses an intraocular lens formed of a polymer having a softening or glass transition temperature less than 42° C. and preferably about body temperature. The lens can be heated to above its softening temperature and deformed by compression or elongation to reduce at least one dimension. Then, by cooling the lens at a temperature substantially below its softening temperature, the lens will remain in the deformed configuration until it is warmed. Ophthalmic surgeons can implant the deformed lens and once the lens warms to body temperature it returns to its original configuration.

A major problem associated with these intraocular lenses is the limited number of polymers available for preparing the lenses. Polymethylmethacrylate has a glass transition temperature of 100° C. and thus cannot be used to form these lenses. Most acrylates and methacrylates have similarly high glass transition temperatures. Though formulating the lenses with plasticizers will lower the glass transition temperature, the presence of plasticizers in intraocular lenses is generally unacceptable to most surgeons because of potential leaching problems. Alternatively, water is a suitable plasticizer. However, only small amounts of water, typically less than 10%, can be utilized in the polymers to place the glass transition in the appropriate range. Thus, typical hydrogels which have much higher amounts of water are not suitable for fabricating the deformable lenses.

An additional drawback with this suggested small incision intraocular lens is the added degree of surgical complexity required to deform the lens into its small incision configuration. The lenses disclosed in U.S. Pat. No. 4,731,079, described above, are packaged in a form that requires the implanting surgeon to warm, deform, and cool the lens immediately prior to its implantation. This procedure is considerably more involved than traditional lens implantation techniques.

Another suggested approach for small incision lens implantation involves implanting hydrogel intraocular lenses in their smaller dehydrated state. Once the implanted dehydrated lens is secured within the eye it reportedly hydrates and swells in the aqueous ocular environment. A significant problem associated with this approach is the large amount of swelling required to produce an effective lens diameter. In order to fully swell the lens from a diameter of about 3 mm to about 6 mm the lens must swell 8 times by volume. This translates to a lens which is about 85% water. For larger full-size intraocular lenses the swell volume is much higher. Since most hydrogels are structurally very weak at these high water contents, many surgeons are reluctant to implant them. Also, these high water content hydrogels have a very low refractive index of around 1.36. In order to achieve suitable refractive powers, the hydrogel lens must therefore be thicker in the optic portion. As a result, a dehydrated hydrogel intraocular lens that will fit through a desirably small incision will not swell to a sufficiently large hydrated size to effectively function as an intraocular lens. This problem is compounded if larger, full size intraocular lenses that have optic diameters greater than 6 mm are desired. In order to produce a hydrated lens having a sufficient optic diameter the dehydrated hydrogel lens must be larger than desirable for a small incision implantation procedure.

Alternatively, U.S. Pat. No. 4,919,662 suggests rolling or folding hydrogel intraocular lenses in their elastic hydrated form, and then dehydrating the lenses at lower temperatures to fix the rolled or folded lens configuration at a size suitable for small incision implantation. Once implanted, these lenses hydrate and swell to the original lens configuration. This method has the disadvantage of requiring the handling of fully hydrated lenses during the deforming process. Unfortunately, hydrated lenses have relatively weak tensile strengths and tear strengths and handling the lenses causes frequent tearing damage.

U.S. Pat. No. 4,813,954 discloses expansile hydrogel intraocular lenses which are formed by simultaneously deforming and dehydrating hydrogel intraocular lenses prior to implanting the lenses in their dehydrated state. Lenses subjected to this treatment swell to about 180% of their reduced size. For example, lenses deformed or compressed to a diameter of 3.2 mm will swell to only about 5.8 mm. Thus, while providing some advantages over simply implanting dehydrated lenses, the method and lenses described in U.S. Pat. No. 4,813,954 do not result in full-size implanted intraocular lenses of over 8 mm.

In addition to size considerations, however, the constitution of the hydrogels must also be considered. The provision of high water content, optically transparent, high refractive index hydrogels which possess long term stability depends to a large extent upon the make-up of the hydrogel. Since most hydrogels are composed of cross-linked copolymers, the selection of appropriate comonomers and cross-linking agents is an important consideration.

It is therefore an object of the present invention to provide cross-linked hydrogels having the properties of high water content, high refractive index, optical transparency, high strength, and long term stability, which hydrogels are biocompatible and suitable for use as intraocular lenses. Another object of this invention is to provide methods for the preparation of such hydrogels.

Other objects and advantages of the present invention will become apparent from the following disclosure and description.

SUMMARY OF THE INVENTION

The present invention accomplishes the above-mentioned objectives by providing a novel series of copolymers in which one of the comonomers is N-benzyl-N-methylacrylamide (BMA), a previously unknown compound. The other comonomer or comonomers may either be derivatives of acrylic acid, such as acrylates, methacrylates, acrylamides or methacrylamides; vinyl-substituted amides; or nitrogen-containing heterocyclic compounds which are substituted with unsaturated sidechains, such as vinyl or acryloyl sidechains.

The copolymers of the present invention upon cross-linking and hydration form optically transparent biocompatible hydrogels which have refractive indices in the dry state of 1.53 to 1.55 and in the fully hydrated state of 1.42 to 1.49. They hydrate to an equilibrium water content in the range of 20% to 65% and are stable for extended periods of time. The resulting hydrogels are stronger than previously available hydrogels and are useful in intraocular lenses and related applications.

Further objects, features and advantages of the present invention, as well as a better understanding thereof, will be afforded to those skilled in the art from a consideration of the following detailed explanation of exemplary embodiments thereof.

DETAILED DESCRIPTION OF THE EXEMPLARY EMBODIMENTS

The present invention provides hydrophilic polymeric materials which form hydrogels. Because of their importance in the field of biomaterials and agriculture, hydrogels and processes for their formation are well documented in the literature.

A preferred class of hydrogel-forming polymers includes cross-linked polymers and copolymers which hydrate to a relatively high hydrated equilibrium water content. As pointed out above, however, high water content hydrogels generally have very low refractive indices. It is, therefore, unexpected to find that cross-linked copolymers of N-benzyl-N-methylacrylamide have equilibrium water contents of 20% to 65% and refractive indices ranging from 1.53 to 1.55 in the dry state and from 1.42 to 1.49 in the fully hydrated state. By using the hydrogels of this invention it is possible to provide higher refractive power in a lens or other article with a much thinner optic portion than by using the low refractive index, high water content hydrogels previously available. It will be appreciated by those skilled in the art that the hydrogels of the present invention can be tailored to provide a wide range of refractive indices and hydrated equilibrium water contents, in order to accommodate a variety of utilities.

N-benzyl-N-methylacrylamide (BMA) is a novel compound. It can be synthesized from N-benzylmethylamine by reaction with acryloyl chloride. N-benzyl-N-methylacrylamide is polymerizable to form a homopolymer which has a water content less than 5% and a refractive index of 1.585. Because of these properties, homopolymers of BMA can be used in hard intraocular lenses and related applications. BMA can also be copolymerized with a wide variety of comonomers to form copolymers which, upon cross-linking and hydration, yield high water content, high refractive index hydrogels having outstanding strength characteristics.

| | |
|---|---|
| alkyl acrylates (alkyl = 1–6 carbon) | 3-(N,N-dimethylamino) propylacrylamide |
| phenyl acrylate | allylacrylamide |
| hydroxyethyl acrylate | hydroxymethyldiacetone-acrylamide |
| hydroxypropyl acrylate | N,N-dimethylacrylamide |
| hydroxybutyl acrylate | N,N-diethylacrylamide |
| glycerol monoacrylate | N-ethyl-N-methylacrylamide |
| 2-phenoxyethyl acrylate | N-methylmethacrylamide |
| 2-N-morpholinoethyl acrylate | N-methylolmethacrylamide |
| 2-(2-ethoxyethoxy)ethyl acrylate | N-(2-hydroxypropyl) methacrylamide |
| 2-(N,N-dimethylamino)ethyl acrylate | N-4-(hydroxyphenyl) methacrylamide |
| 3-(N,N-dimethylamino)propyl acrylate | N-(3-picolyl)methacrylamide |
| alkyl methacrylates (alkyl = 1–6 carbon) | 3-vinylpyridine |
| furfuryl methacrylate | 4-vinylpyridine |
| hydroxyethyl methacrylate | N-vinylpyrrolidinone |
| hydroxypropyl methacrylate | vinyl pyrazine |
| hydroxybutyl methacrylate | 2-methyl-5-vinylpyrazine |
| glycerol monomethacrylate | 4-vinylpyrimidine |
| 2-phenoxyethyl methacrylate | vinyl pyridazine |
| 2-N-morpholinoethyl methacrylate | N-vinylimidazole |
| 2-(N,N-dimethylamino)ethyl methacrylate | N-vinylcarbazole |
| 3-(N,N-dimethylamino)propyl methacrylate | N-vinylsuccinimide |
| 2-pyrrolidinonylethyl methacrylate | 4-methyl-5-vinylthiazole |
| N-alkyl acrylamides (alkyl = 1–8 carbon) | N-acryloylmorpholine |
| N-(n-octadecylacrylamide) | N-methyl-N-vinylacetamide |

Cross-linking agents which can be used to produce the hydrogels of the present invention include 1,3-propanediol diacrylate, 1,4-butanediol diacrylate, 1,6-hexamethylene diacrylate, 1,4-phenylene diacrylate, glycerol tris (acryloxypropyl) ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylene-bisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

In general, BMA is present in an amount of about 5 weight percent to 85 weight percent based on the total weight of monomers. The cross-linking agent may be used in an amount of about 0.01 weight percent to 0.50 weight percent.

The hydrogels of the present invention may also include from about 0.1 weight percent to about 10 weight percent ultraviolet (UV) radiation absorbing compounds. A large variety of hydroxybenzophenones and hydroxyphenylbenzotriazoles are commercially available and may be used for this purpose. Preferably, the UV-absorbing compound is copolymerizable with the monomer forming the hydrogel polymer, thus becoming part of the final polymer or copolymer. This feature assures that the hydrated hydrogel is optically clear, and assures that the UV-absorbing compound does not leach or migrate from the article fabricated from the hydrogel, for example, from an implanted lens. An exemplary UV-absorber of this type is 2-(2'-hydroxy-5'-methacryloxyethylphenyl)-2H-benzotriazole. In addition, the allyloxypropyl modified hydroxyphenylbenzotriazole, 2-[5-chloro-2H-benzotriazol-2-yl]-6-[1,1-dimethylethyl]-4-[2-propenyloxypropyl] phenol, known as Tinuvin 326, is particularly suitable because of its high absorptivity at wavelengths up to 405 nm, its solubility, and its vinyl functionality.

The relative amounts of the various comonomers and other reagents used to produce the hydrogel-forming materials will depend upon the desired strength, final water content, and refractive index, as well as the amount of material elasticity required to deform a lens fabricated of the hydrogel or to otherwise apply the hydrogel to a specific application. The hydrogel materials also should have sufficient resiliency at their deformation temperatures to prevent permanent stretching or cracking during or after any deforming process.

Hydrogels prepared using BMA have the properties desired for use in a wide variety of applications, especially those applications requiring high strength, high hydrophilicity and long term stability. For example, the hydrogels thus prepared can be used to produce polyelectrolyte gels, high water content superabsorbents, contact lenses, cornea on-lays, cornea in-lays, and other medical devices requiring these properties, as well as intraocular lenses.

The following examples are offered as being illustrative of the principles of the present invention and not by way of limitation.

EXAMPLE 1

Synthesis of N-benzyl-N-methylacrylamide

A quantity of 121 g of N-benzylmethylamine was reacted with 100 g of acryloyl chloride in the presence of 111 g of triethylamine in ether at 0° C. to 25° C. for 16 hours. The product was filtered, the solvent was removed, and N-benzyl-N-methylacrylamide was isolated in 69% yield by distillation under vacuum Cop 83°–85° C./0.04 mm—Hg).

The following example illustrates the polymerization of N-benzyl-N-methyl-acrylamide and various other monomers.

EXAMPLE 2

Eleven different homopolymers and copolymers were prepared and evaluated for use as exemplary hydrogel-forming materials. Table I illustrates the proportions of each component of the polymerization mixture and the properties of the polymers obtained. Each polymerization procedure was carried out by first mixing the appropriate amounts of the monomers and cross-linker, if any, with 2,2'-azobisisobutyronitrile as a polymerization initiator. Then each mixture was transferred to an ampoule which was pretreated with a silicone grease mold releasing agent. Each ampoule and mixture was then attached to a vacuum system and cooled with liquid nitrogen. After the mixture was frozen by the liquid nitrogen, the mixture was evacuated by turning on the vacuum system. Once a constant pressure was achieved, the vacuum system was turned off and the mixture was allowed to thaw by warming the ampoule in a water bath. This freeze-thaw cycle was repeated three times in order to provide sufficient mixture degassing. Finally, each mixture and ampoule were sealed under vacuum or an inert gas such as nitrogen or argon and polymerized at a temperature of 60° C. for a period of 36 hours, then at 135° C. for 12 hours.

After the polymerized material was cooled, the ampoule was broken open and the resulting polymer rod was cut into blanks. Each blank was then machined to an expansile intraocular lens in its dehydrated state. The machined dehydrated lenses have diameters ranging from approximately 4.5 to 7.1 mm and cross-sectional thicknesses ranging from approximately 2.3 to 3.6 mm.

Exemplary lenses were deformed by heating a water bath to 60° C. and placing a beaker of heptane in the water bath. The lenses were immersed in the warm heptane for approximately 10 seconds and simultaneously folded with a pair of tweezers. The folded lenses were then removed from the heptane and inserted into $\frac{1}{16}$ inch I.D. silicone tubes. The tubes and folded lenses were then immersed in the warm heptane for 10–20 seconds. The tubes and lenses were removed from the heptane and immediately rolled and squeezed between two fingers, compressing the lenses into tightly folded and elongated shapes. The elongated lenses and tubes were allowed to cool to room temperature and then the lenses were removed from the tubes. At room temperature the lenses remained in their elongated state. The long dimension ranges from approximately 8 to 13 mm, the cross-sectional width ranges from approximately 2 to 4 mm, and the cross-sectional height ranges from approximately 1.8 to 3.0 mm.

Each lens was immersed in physiologically buffered aqueous solutions for 8–48 hours and allowed to hydrate to its equilibrium water content. The lenses were observed to expand and re-form to the original configuration. The enlarged reconfigured hydrated lenses have expanded diameters ranging from approximately 8.5 to 9.5 mm and expanded cross-sectional thicknesses of approximately 4.5 mm.

The abbreviations utilized in Table I are identified immediately following the table.

TABLE I

| Exper-iment No. | BMA | DMA | NVP | HEMA | PEMA | DEA | BEA | EGDMA | UV-ABSORBER | $n_D^{37}$ Dry | $n_D^{37}$ Wet | Tensile (psi) | Tear (pli) | Elongation % | Durometer Shore A | $H_2O$ % |
|---|---|---|---|---|---|---|---|---|---|---|---|---|---|---|---|---|
| 1 |  | 100 |  |  |  |  |  |  |  | 1.51 | 1.34 |  |  |  |  | >98 |
| 2 | 5 | 45 |  | 50 |  |  |  | 0.01 |  | 1.52 | 1.39 |  |  |  |  | 65 |
| 3 | 33.4 | 65.2 |  |  |  |  |  | 0.34 | 1 | 1.535 | 1.42 | 18 | 2 | 330 |  | 57 |
| 4 |  |  |  | 100 |  |  |  |  |  | 1.51 | 1.44 |  |  |  |  | 39 |
| 5 | 30 | 35 |  | 35 |  |  |  | 0.02 | 2 | 1.535 | 1.46 | 75 | 9 | 440 | 12 | 36 |
| 6 | 22 | 10 |  | 68 |  |  |  | 0.17 | 2 | 1.532 | 1.482 | 180 | 45 | 150 | 27 | 24 |
| 7 | 25 | 5 |  | 70 |  |  |  | 0.4 | 2 | 1.535 | 1.49 | 320 | 83 | 230 | 31 | 22 |
| 8 | 100 |  |  |  |  |  |  |  |  | 1.585 | 1.58 |  |  |  |  | <5 |
| 9 | 85 | 15 |  |  |  |  |  |  |  |  |  |  |  |  |  |  |
| 10 | 60 | 40 |  |  |  |  |  |  |  |  |  |  |  |  |  |  |
| 11 | 10 | 50 |  | 40 |  |  |  |  |  |  |  |  |  |  |  |  |
| 12 | 34 | 19 | 20 | 27 |  |  |  | 0.15 | 1.2 | 1.542 |  |  |  |  |  | 34 |
| 13 | 38 | 31 |  | 24 | 7 |  |  | 0.04 | 1.2 | 1.542 |  |  |  |  |  | 30 |
| 14 | 40 |  |  |  |  | 60 |  | 0.01 | 1.4 |  |  |  |  |  |  |  |
| 15 |  |  |  |  |  | 69 | 31 | 0.01 | 1.4 |  |  |  |  |  |  |  |
| 16 | 43 | 49 |  |  |  |  | 8 | 0.01 | 1.2 | 1.547 |  |  |  |  |  | 38 |
| 17 | 38 | 45 |  |  |  | 17 |  | 0.01 | 1.2 | 1.541 |  |  |  |  |  | 43 |

BEA N-benzyl-N-ethylacrylamide
BMA N-benzyl-N-methylacrylamide
DEA N,N-diethylacrylamide
DMA N,N-dimethylacrylamide
EGDMA ethylene glycol dimethacrylate
HEMA 2-hydroxyethyl methacrylate
UV-ABSORBER 2-(2'-hydroxy-5'-methacrylyloxyethylphenyl)-2H-benzotriazole
NVP N-vinylpyrrolidinone
PEMA 2-pyrrolidinonylethyl methacrylate Because of the outstanding properties of hydrogels produced using the novel monomers of the present invention including their optical transparency, their high water content, and their high refractive index, they display extremely good optical resolution efficiency.

Thus, the use of the novel monomers of the present invention results in hydrogels which display excellent optical properties, as well as excellent stability.

Having thus described exemplary embodiments of the present invention, it should be noted by those skilled in the art that the disclosures herein are exemplary only and that alternatives, adaptations, and modifications may be made within the scope of the present invention.

What is claimed is:

1. A hydrogel comprising a cross-linked copolymer prepared from a mixture of comonomers comprising N-benzyl-N-methylacrylamide and at least one comonomer polymerizable with said N-benzyl-N-methylacrylamide.

2. The hydrogel of claim 1 wherein said at least one comonomer polymerizable with said N-benzyl-N-methylacrylamide is selected from the group consisting of acrylates, methacrylates, acrylamides, methacrylamides, vinyl-substituted amides, vinyl-substituted nitrogen-containing heterocyclic compounds, and acryloyl-substituted nitrogen-containing heterocyclic compounds.

3. The hydrogel of claim 1 wherein said at least one comonomer polymerizable with said N-benzyl-N-methylacrylamide is selected from the group consisting of methyl acrylate, ethyl acrylate, propyl acrylate, butyl acrylate, amyl acrylate, hexyl acrylate, phenyl acrylate, hydroxyethyl acrylate, hydroxypropyl acrylate, hydroxybutyl acrylate, glycerol monoacrylate, 2-phenoxyethyl acrylate, 2-N-morpholinoethyl acrylate, 2-(2-ethoxyethoxy) ethyl acrylate, 2-(N,N-dimethylamino)ethyl acrylate, 3-(N, N-dimethylamino)propyl acrylate, methyl methacrylate, ethyl methacrylate, propyl methacrylate, butyl methacrylate, amyl methacrylate, hexyl methacrylate, furfuryl methacrylate, hydroxyethyl methacrylate, hydroxypropyl methacrylate, hydroxybutyl methacrylate, glycerol monomethacrylate, 2-phenoxyethyl methacrylate, 2-N-morpholinoethyl methacrylate, 2-(N,N-dimethylamino) ethyl methacrylate, 3-(N,N-dimethylamino)propyl methacrylate, 2-pyrrolidinonylethyl methacrylate, N-methylacrylamide, N-ethylacrylamide, N-propylacrylamide, N-butylacrylamide, N-amylacrylamide, N-hexylacrylamide, N-heptylacrylamide, N-octylacrylamide, N-(n-octadecylacrylamide), 3-(N,N-dimethylamino) propylacrylamide, allylacrylamide, hydroxymethyldiacetoneacrylamide, N,N-dimethylacrylamide, N,N-diethylacrylamide, N-ethyl-N-methylacrylamide, N-methylmethacrylamide, N-methylolmet.hacrylamide, N-(2-hydroxypropyl) methacrylamide, N-4-(hydroxyphenyl)methacrylamide, N-(3-picolyl)methacrylamide, 3-vinylpyridine, 4-vinylpyridine, N-vinylpyrrolidinone, vinyl pyrazine, 2-methyl-5-vinylpyrazine, 4-vinylpyrimidine, vinyl pyridazine, N-vinylimidazole, N-vinylcarbazole, N-vinylsuccinimide, 4-methyl-5-vinylthiazole, N-acryloylmorpholine, and N-methyl-N-vinylacetamide.

4. The hydrogel of claim 1 wherein said at least one comonomer polymerizable with said N-benzyl-N-methylacrylamide is selected from the group consisting of N,N-dimethylacrylamide, N,N-diethylacrylamide, 2-hydroxyethyl methacrylate, N-vinylpyrrolidinone, and 2-pyrrolidinonylethyl methacrylate.

5. The hydrogel of claim 1 wherein said mixture of comonomers includes a cross-linking agent selected from the group consisting of 1,3-propanediol diacrylate, 1,4-butanediol diacrylate, 1,6-hexamethylene diacrylate, 1,4-phenylene diacrylate, glycerol tris (acryloxypropyl) ether, ethylene glycol dimethacrylate, 1,3-propanediol dimethacrylate, 1,6-hexamethylene dimethacrylate, 1,10- decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

6. The hydrogel of claim 2 wherein said mixture of comonomers includes a cross-linking agent selected from the group consisting of 1,3-propanediol diacrylate, 1,4-butanediol diacrylate, 1,6-hexamethylene diacrylate, 1,4-phenylene diacrylate, glycerol tris (acryloxypropyl) ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

7. The hydrogel of claim 3 wherein said mixture of comonomers includes a cross-linking agent selected from the group consisting of 1,3-propanediol diacrylate, 1,4-butanediol diacrylate, 1,6-hexamethylene diacrylate, 1,4-phenylene diacrylate, glycerol tris (acryloxypropyl) ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

8. The hydrogel of claim 4 wherein said mixture of comonomers includes a cross-linking agent selected from the group consisting of 1,3-propanediol diacrylate, 1,4-butanediol diacrylate, 1,6-hexamethylene diacrylate, 1,4-phenylene diacrylate, glycerol tris (acryloxypropyl) ether, ethylene glycol dimethacrylate, 1,3-propanediol dimethacrylate, 1,6-hexamethylene dimethacrylate, 1,10-decanediol dimethacrylate, 1,12-dodecanediol dimethacrylate, triethylene glycol dimethacrylate, glycerol trimethacrylate, N,N'-octamethylenebisacrylamide, N,N'-dodecanomethylenebisacrylamide, N,N'-(1,2-dihydroxyethylene)bisacrylamide, allyl methacrylamide, divinylpyridine, 4,6-divinylpyrimidine, 2,5-divinylpyrazine, 1,4-divinylimidazole, 1,5-divinylimidazole, and divinylbenzene.

9. An intraocular lens fabricated from the hydrogel of claim 1.

10. An intraocular lens fabricated from the hydrogel of claim 2.

11. An intraocular lens fabricated from the hydrogel of claim 3.

12. An intraocular lens fabricated from the hydrogel of claim 4.

13. An intraocular lens fabricated from the hydrogel of claim 5.

14. An intraocular lens fabricated from the hydrogel of claim 6.

15. An intraocular lens fabricated from the hydrogel of claim 7.

16. An intraocular lens fabricated from the hydrogel of claim 8.

17. The hydrogel of claim 1 having a refractive index, $n_D^{37}$, of 1.53 to 1.55 in the dry state and 1.42 to 1.49 in the fully hydrated state.

18. The hydrogel of claim 1 having an equilibrium water content of 20% to 65%.

* * * * *